US006994702B1

(12) United States Patent
Johnson

(10) Patent No.: US 6,994,702 B1
(45) Date of Patent: Feb. 7, 2006

(54) VACUUM ASSISTED CLOSURE PAD WITH ADAPTATION FOR PHOTOTHERAPY

(75) Inventor: Royce W. Johnson, Universal City, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 09/544,399

(22) Filed: Apr. 6, 2000

Related U.S. Application Data

(60) Provisional application No. 60/127,936, filed on Apr. 6, 1999.

(51) Int. Cl.
*A61B 18/18* (2006.01)

(52) U.S. Cl. .............................. 606/9; 606/14; 607/88

(58) Field of Classification Search ................ 604/313, 604/307; 606/27, 2, 3, 9, 115, 88, 11, 14, 606/16, 13; 607/115, 101, 88, 89; 601/152
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,969,057 | A | 1/1961 | Simmons |
| 3,367,332 | A | 2/1968 | Groves |
| 3,520,300 | A | 7/1970 | Flower |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |

(Continued)

FOREIGN PATENT DOCUMENTS

AU 550575 A1 8/1982

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, ...

(Continued)

*Primary Examiner*—Larry I. Schwartz
*Assistant Examiner*—M G. Bogart

(57) ABSTRACT

A modified vacuum assisted wound closure system adapted for concurrent applications of phototherapy having a foam pad for insertion substantially into the wound site and a wound drape for sealing enclosure of the foam pad at the wound site. The foam pad includes an optical pigtail, whereby desired wavelength of light may be directed into and about the wound site. The foam pad is placed in fluid communication with a vacuum source for promotion of fluid drainage. The foam pad is made of a highly reticulated, open-cell polyurethane or polyether foam for good permeability of wound fluids while under suction and is also embedded with an optical pigtail. The optical pigtail comprises an optical fiber that has been formed to fan into a plurality of sections. The fibers of the most distal fanned sections, which are implanted in the foam pad at its base, are provided with tiny optical slots, oriented away from the foam pad and toward the wound site. Each optical slot is made by stripping the cladding from the optical fiber in the desired areas of the fanned sections to form slot radiators. Because it is necessary to trim the foam pad in preparation for therapy, the optical fibers comprise plastics, such as acrylic or styrene. Upon placement of the pad, having the optical pigtail embedded therein, the wound drape is firmly adhered about the VAC therapy suction hose as well as the extending optical fiber to prevent vacuum leakage.

9 Claims, 1 Drawing Sheet

U.S. PATENT DOCUMENTS

| | | | |
|---|---|---|---|
| 4,096,853 A | 6/1978 | Weigand | |
| 4,139,004 A | 2/1979 | Gonzalez | |
| 4,165,748 A | 8/1979 | Johnson | |
| 4,233,969 A | 11/1980 | Lock et al. | |
| 4,245,630 A | 1/1981 | Lloyd et al. | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,949 A | 5/1989 | Stanko | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,702 A * | 11/1990 | Anderson | 350/96.2 |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,100,429 A * | 3/1992 | Sinofsky et al. | 623/1.21 |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,344,415 A | 9/1994 | DeBusk et al. | |
| 5,358,494 A | 10/1994 | Svedman | |
| 5,358,503 A * | 10/1994 | Bertwell et al. | 606/27 |
| 5,437,622 A | 8/1995 | Carion | |
| 5,437,651 A | 8/1995 | Todd et al. | |
| 5,474,528 A * | 12/1995 | Meserol | 604/20 |
| 5,527,293 A | 6/1996 | Zamierowski | |
| 5,549,584 A | 8/1996 | Gross | |
| 5,556,375 A | 9/1996 | Ewall | |
| 5,584,296 A * | 12/1996 | Cui et al. | 600/479 |
| 5,607,388 A | 3/1997 | Ewall | |
| 5,636,643 A | 6/1997 | Argenta et al. | |
| 5,645,081 A | 7/1997 | Argenta et al. | |
| 5,766,233 A * | 6/1998 | Thiberg | 607/88 |
| 5,976,175 A * | 11/1999 | Hirano et al. | 607/89 |
| 6,071,267 A * | 6/2000 | Zamierowski | 604/289 |
| 6,128,797 A * | 10/2000 | Shaffer | 5/638 |
| 6,135,116 A * | 10/2000 | Vogel et al. | 128/898 |
| 6,142,982 A * | 11/2000 | Hunt et al. | 604/313 |
| 6,159,236 A * | 12/2000 | Biel | 607/92 |
| 6,168,591 B1 * | 1/2001 | Sinofsky | 606/15 |
| 6,187,029 B1 * | 2/2001 | Shapiro et al. | 607/88 |
| 6,345,623 B1 | 2/2002 | Heaton et al. | |
| 6,350,168 B1 * | 2/2002 | Kroll et al. | 441/111 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0111537 A1 * | 8/2002 | Taylor et al. | 600/210 |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0187486 A1 * | 10/2003 | Savage et al. | 607/89 |
| 2005/0010270 A1 * | 1/2005 | Laufer | 607/88 |

FOREIGN PATENT DOCUMENTS

| | | |
|---|---|---|
| AU | 745271 | 3/2002 |
| AU | 755496 | 12/2002 |
| CA | 2005436 | 6/1990 |
| DE | 26 40 413 A1 | 3/1978 |
| DE | 43 06 478 A1 | 9/1994 |
| DE | 295 04 378 U1 | 9/1995 |
| EP | 0117632 A2 | 1/1984 |
| EP | 0100148 | 2/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 197 789 A | 6/1988 |
| GB | 2333965 A | 8/1999 |
| GB | 2329127 B | 8/2000 |
| SG | 71559 | 4/2002 |
| WO | WO 80/02182 | 10/1980 |
| WO | WO 93/09727 | 5/1993 |
| WO | WO/94/20041 | 9/1994 |
| WO | WO 96/05873 | 2/1996 |
| WO | WO 97/18007 | 5/1997 |
| WO | WO 97/13793 | 9/1997 |
| WO | WO 99/13793 | 9/1998 |

OTHER PUBLICATIONS

Susan Mendez-Eastman, RN; When Wounds Won't Heal, RN Jan. 1998, vol. 61(1); Medical Economics Company, Inc., Montvale, NJ, USA.

James H. Blackburn, II, MD. et al; Negative-Pressure Dressings as a Bolster for Skin Grafts; Annals of Plastic Surgery, vol. 40, No. 5, May 1998, pp. 453-457;....

Johm Masters; Letter to the editor; British Journal of Plastic Surgery, 1998, vol. 51(3), p. 267; Elsevier Science/The British Association of Plastic Surgeons, UK.

S.E. Greer, et al; The Use of Subatmospheric Pressure Dressing Therapy to Clos Lymphocutaneous Fistulas of the Groin; British Journal of Plastic Surgery (2000), 53....

George V. Letsou, M.D., et al; Stimulation of Adenylate Cyclase Activity in Cultured Endothelial Cells Subjected to Cyclic Stretch; Journal of Cardiovascular Surgery, 31, 1990.

PCT International Search Report; PCT international application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/02802; Sep. 3, 1997.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts For the Clinical-Biological Management of the Wound Process in the Treatment of Purulent Wounds by Means of Vacuum Therapy; Vestnik Khirurgi.

International Search Report for PCT international application PCT/GB95/01983; Nov. 23, 1995.

Patent Abstract of Japan; JP4129536; Terumo Corporation; Apr. 30, 1992.

Orringer, Jay, et al., "Management of Wounds in Patients with Complex Enterocutaneous Fistulas", Surgery, Gynecology & Obstertics, Jul. 1987, V. 165, pp. 79-80.

* cited by examiner

VACUUM ASSISTED CLOSURE PAD WITH ADAPTATION FOR PHOTOTHERAPY

RELATED APPLICATION

The present invention claims the benefit, under 35 U.S.C. § 119(e), of the filing of U.S. provision patent application Ser. No. 60/127,936 filed Apr. 6, 1999.

BACKGROUND OF THE INVENTION

1. Field of the Invention

The present invention relates to the healing of wounds. More particularly, the invention relates to a vacuum assisted wound closure system wherein a foam pad is modified to facilitate wound healing by including phototherapy compatible optical fibers.

2. Background of the Invention

Wound closure involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion, whereafter cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but are also less able to successfully fight bacterial infection and thus are less able to naturally close the wound. Until recently, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples causes very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative gauge pressure, commercialized by Applicant under the designation "Vacuum Assisted Closure" (or "V.A.C.") therapy, typically involves the mechanical-like contraction of the wound with simultaneous removal of excess fluid. In this manner, VAC therapy augments the body's natural inflammatory process while alleviating many of the known intrinsic side effects, such as the production of edema caused by increased blood flow absent the necessary vascular structure for proper venous return.

While V.A.C.® therapy has been highly successful in the promotion of wound closure, healing many wounds previously thought largely untreatable, some difficulty remains. Because the very nature of V.A.C. therapy dictates an atmospherically sealed wound site, the therapy must often be performed to the exclusion of other beneficial, and therefore desirable, wound treatment modalities. One such excluded modality is phototherapy—a method for wound treatment wherein appropriate wavelengths of light are directed into or about the wound bed.

Phototherapy has to date been regarded as impossible or at least impracticable in combination with V.A.C. therapy due to the utilization of opaque materials in the administration of V.A.C. therapy. In particular, the use of an opaque foam pad for within the wound site, as is known to those of ordinary skill in the V.A.C.-related arts, requires that the V.A.C. therapy be disrupted and the dressings removed in order that phototherapy can be performed. Because phototherapy and the like are nonetheless desirable in combination with V.A.C. therapy, it is a primary object of the present invention to provide a V.A.C. therapy wound dressing that is compatible with such therapies.

It is a further object of the present invention to provide such a dressing that is also readily adaptable to a variety of wound sizes and shapes and that requires no inordinate modification of known procedures for or administration of V.A.C. therapy.

It is yet a further object of the present invention to provide such a dressing that is economical and disposable, but also safe for general patient use.

SUMMARY OF THE INVENTION

In accordance with the foregoing objects, the present invention—a modified vacuum assisted wound closure system adapted for concurrent applications of phototherapy—generally comprises a foam pad for insertion substantially into the wound site and a wound drape for sealing enclosure of the foam pad at the wound site. According to the invention, the foam pad is modified to comprise an optical pigtail, whereby a desired wavelength of light may be directed into and about the wound site. Although the foam pad is placed in fluid communication with a vacuum source for promotion of fluid drainage, as known in the art, the addition of the optical pigtail is noninvasive to the known V.A.C. therapy and requires no modification thereof.

According to the preferred embodiment of the present invention, the foam pad preferably comprises a highly reticulated, open-cell polyurethane or polyether foam for good permeability of wound fluids while under suction, as previously known in the art. However, the foam pad of the present invention is also provided with an optical pigtail. This optical pigtail comprises an optical fiber that has been formed to fan into a plurality of sections, much like a capillary vessel system. The fibers of the most distal fanned sections, which are implanted in the foam pad at its base, are provided with tiny optical slots, preferably oriented away from the foam pad and toward the wound site.

Each optical slot is made by stripping the cladding from the optical fiber in the desired areas of the fanned sections. In this manner, the slots form slot radiators, each of which is thereby adapted to illuminate a portion of the wound site.

Because it is often necessary to trim the foam pad in ordinary preparation for V.A.C. therapy wound treatment, the optical fibers preferably comprise plastic cores and claddings, which is appropriate for those wavelengths in the visible and near infrared as are typically utilized in phototherapy applications. One such material as may be employed is acrylic, which is inexpensive and easy to cut, but those of ordinary skill in the art will recognize many substantial equivalents, such as styrene, which although more expensive and brittle, may also suffice if an ultraviolet application is required. Other materials and adaptations may be utilized in alternative embodiments. The particulars of such alternatives will depend on the particularities of the applications and on the wavelength, intensity and other properties of the electromagnetic energy being delivered in conjunction with the V.A.C. therapy.

Upon placement of the pad, having the optical pigtail embedded therein, the wound drape is firmly adhered about the V.A.C. therapy suction hose as well as the extending optical fiber to prevent vacuum leakage. In use the V.A.C. therapy is conducted as known and, if desired, phototherapy is added by simply illuminating the optical slot radiators through the fiber. In this manner, phototherapy may be conveniently combined with existing V.A.C. therapies, without loss of V.A.C. therapy performance and without inconvenience or overly increased cost.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Figure 1:
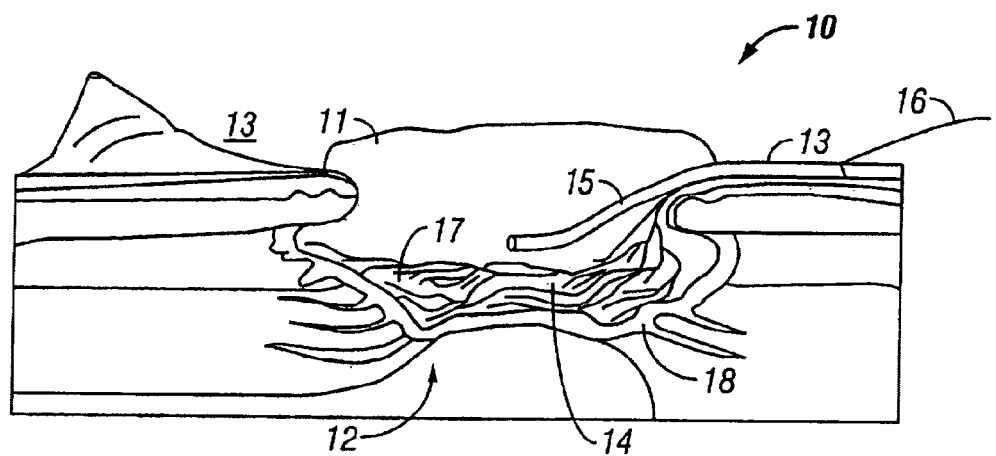
FIG. 1 shows, in partially cut away perspective view, the preferred embodiment of the present invention as applied to a mammalian wound site.

Although those of ordinary skill in the art will readily recognize many alternative embodiments, especially in light of the illustrations provided herein, this detailed description is exemplary of the preferred embodiment of the present invention, the scope of which is limited only by the claims which may be drawn hereto.

Referring now to the figures, the present invention 10 is shown to generally comprise a foam pad 11 for insertion substantially into the wound site 12 and a wound drape 13 for sealing enclosure of the foam pad 11 at the wound site 12. According to the invention, the foam pad 11 is modified to comprise an optical pigtail 14, whereby a desired wavelength of light, within a significant portion of the spectrum between approximately 300 nm and approximately 1500 nm, may be directed into and about the wound site 12. After insertion into the wound site 12 and sealing with the wound drape 13, the foam pad 11 is placed in fluid communication with a vacuum source for promotion of fluid drainage, as known to those of ordinary skill in the art. Although the foam pad 11 is modified from prior art pads in that the pad 11 of the present invention comprises the optical pigtail 14, the optical pigtail 14 is noninvasive to the known V.A.C. therapy and requires no modification thereof.

According to the preferred embodiment of the present invention, the foam pad 11, wound drape 13 and vacuum source are implemented as known in the prior art, with the exception of those modifications to the foam pad 11 detailed further herein. Each of these components is detailed in U.S. patent application Ser. No. 08/517,901 filed Aug. 22, 1995. By this reference, the full specification of U.S. patent application Ser. No. 08/517,901 ("the '901 application"), including the claims and the drawings, is incorporated herein as though now set forth in its entirety.

As detailed in the '901 application, the foam pad 11 preferably comprises a highly reticulated, open-cell polyurethane or polyether foam for good permeability of wound fluids while under suction. As also detailed in the '901 application, the foam pad 11 is preferably placed in fluid communication, via a plastic or like material hose 15, with a vacuum source, which preferably comprises a canister safely placed under vacuum through fluid communication, via an interposed hydrophobic membrane filter, with a vacuum pump. Finally, the '901 application also details the wound drape 13, which preferably comprises an elastomeric material at least peripherally covered with a pressure sensitive, acrylic adhesive for sealing application over the wound site 12.

Figure 2:
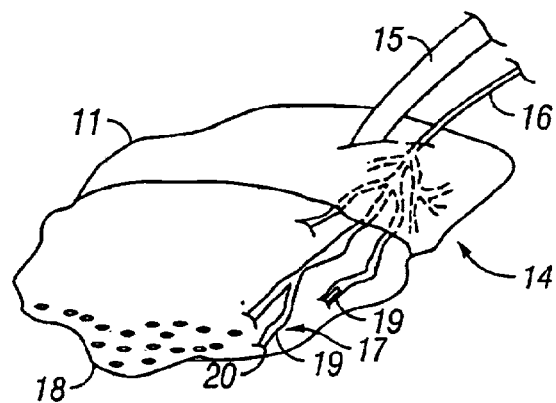
FIG. 2 shows, in partially cut away perspective view, the modified foam pad of the invention of FIG. 1.

According to the preferred method of the present invention, those components as are described in the '901 application are generally employed as known in the art with the exception that the foam pad 11 is provided with an optical pigtail 14. Referring to FIG. 2, this optical pigtail is shown to comprise an optical fiber 16 that has been formed to fan into a plurality of sections 17, much like a capillary vessel system. The fibers of the most distal fanned sections 17, which are implanted in the foam pad 11 at the base 18 of the pad 11, are provided with tiny optical slots 19. Preferably, the provided slots 19 are oriented away from the foam pad 11, toward the wound site 12 when the pad 11 is in place.

Each optical slot 19 is made by stripping the cladding from the optical fiber 16 in the desired areas of the fanned sections 17. In this manner, the slots 19 form slot radiators 20, each of which is thereby adapted to illuminate a portion of the wound site 12. Because it is necessary to trim the foam pad 11 in preparation for V.A.C. therapy wound treatment, the optical fibers 16 preferably comprise plastic cores and claddings, which is appropriate for those wavelengths in the visible and near infrared as are typically utilized in phototherapy applications. One such material as may be employed is acrylic, which is inexpensive and easy to cut, but those of ordinary skill in the art will recognize many substantial equivalents, such as styrene, which although more expensive and brittle, may also suffice if an ultraviolet application is required.

Upon placement of the pad 11, having the optical pigtail 14 embedded therein, the wound drape 13 is firmly adhered about the V.A.C. therapy hose 15 as well as the extending optical fiber 16 to prevent vacuum leakage. In use the V.A.C. therapy is conducted as known and, if desired, phototherapy is added by simply illuminating the optical slot radiators 20 through the fiber 16. In this manner, phototherapy may be conveniently combined with existing V.A.C. therapies, without loss of V.A.C. therapy performance and without inconvenience or overly increased cost.

While the foregoing description is exemplary of the preferred embodiment of the present invention, those of ordinary skill in the relevant arts will recognize the many variations, alterations, modifications, substitutions and the like as are readily possible, especially in light of this description and the accompanying drawings. For example, the known foam pad 11 as presently implemented may be entirely replaced with a plasticized, acrylimide foam, whereby light may be directly transferred therethrough and into the wound site 12. Other embodiments may utilize an electrical current through a coiled conductor (or other form of electromagnetic energy emitter) coupled with or embedded in pad 11 in order to generate any desired form of electromagnetic energy. In any case, because the scope of the present invention is much broader than any particular embodiment, the foregoing detailed description should not be construed as a limitation of the scope of the present invention, which is limited only by the claims that may be drawn hereto.

What is claimed is:

1. A pad for insertion into a wound bed, said pad comprising:
    a reticulated open-cell plasticized acrylmide foam; and
    a means for providing phototherapy.

2. A pad for insertion into a wound bed, said pad comprising:
    comprises a highly reticulated, open cell foam selected from the group consisting of polyurethane and polyether; and
    a means for providing phototherapy.

3. A pad for insertion into a wound bed, said pad comprising:
    a highly reticulated open-cell foam; and
    an optical pigtail for providing phototherapy.

4. A pad according to claim 3 wherein said pigtail comprising a plurality of optical fibers.

5. A wound healing apparatus comprising:
    a reticulated open-cell foam pad for insertion into a wound bed;
    a means for providing phototherapy; and
    a device enabling the concurrent application of negative pressure therapy and the delivery of electromagnetic energy to a wound, wherein said device comprises a vacuum drainage means, an air tight drape providing a seal about said pad, and an energy integrally incorporated within said pad.

6. A wound healing apparatus according to claim 5 wherein said energy emitter comprises optical slots.

7. A method of providing concurrent negative pressure therapy and phototherapy comprising negative pressure application means having phototherapy means integrated therein.

8. A method according to claim 7 wherein said phototherapy means comprises optical slots.

9. A pad for use in negative pressure therapy also comprise means for providing phototherapy, said pad comprised of a plasticized, acrylamide foam, and wherein said pad transmits electromagnetic radiation in a significant portion of the spectrum between about 300 nm and approximately 1500 nm.

\* \* \* \* \*

UNITED STATES PATENT AND TRADEMARK OFFICE
CERTIFICATE OF CORRECTION

PATENT NO. : 6,994,702 B1
APPLICATION NO. : 09/544399
DATED : February 7, 2006
INVENTOR(S) : Royce W. Johnson Page 1 of 1

It is certified that error appears in the above-identified patent and that said Letters Patent is hereby corrected as shown below:

Title Page
(54) the title should read --Negative Pressure Wound Therapy Pad with Adaptation for Phototherapy--
Column 5, line 25 delete "comprises"
Column 5, line 25 replace "open cell" with --open-cell--
Column 6, line 4 replace "comprising" with --comprises--
Column 6, line 13 add --emitter-- after "energy"
Column 6, line 23 add --that-- after "therapy"
Column 6, line 23/24 replace "comprise" with --comprises--

Signed and Sealed this

Nineteenth Day of September, 2006

JON W. DUDAS
*Director of the United States Patent and Trademark Office*